United States Patent [19]

Inoue et al.

[11] 4,129,649

[45] Dec. 12, 1978

[54] PROCESS FOR PRODUCING EASILY ABSORBABLE AMORPHOUS STERYL GLUCOSIDE MONOPALMITATES AND PREPARATIONS THEREOF

[75] Inventors: Sho Inoue; Masanobu Kawamata; Hirokazu Ushimaru; Koichi Nakamichi; Yutaka Takahashi, all of Kyoto, Japan

[73] Assignee: Nippon Shinyaku Co. Ltd., Japan

[21] Appl. No.: 683,478

[22] Filed: May 5, 1976

[30] Foreign Application Priority Data

May 24, 1975 [JP] Japan .................................. 50-62263

[51] Int. Cl.² .................... A61K 31/705; C07G 3/00
[52] U.S. Cl. ........................................ 424/182; 536/5
[58] Field of Search .................. 260/210.5, 707; 424/182, 180; 536/1, 4, 5, 6

[56] References Cited

U.S. PATENT DOCUMENTS

| | | | |
|---|---|---|---|
| 2,746,957 | 5/1956 | Perlman et al. | 536/5 |
| 3,036,060 | 5/1962 | Lucas et al. | 536/5 |
| 3,238,104 | 3/1966 | Madaus et al. | 260/210.5 |
| 3,753,975 | 8/1973 | Kaiser | 424/182 |

OTHER PUBLICATIONS

Kirk–Ohmer, "Encylop. of chemical Technology", Crystalization, pp. 492–493, vol. 6, 2nd Ed., 1965, Wiley & Sons, Inc.
Kisilev et al., "On Phase Transformations of Dextran", Chem. Abst., vol. 84, 1976, p. 137553M.
Kirk–Othmer, "Encyclopedia of Chem Tech.", vol. 13, pp. 212–213.

*Primary Examiner*—Henry R. Jiles
*Assistant Examiner*—Cary Owens
*Attorney, Agent, or Firm*—Jacobs & Jacobs

[57] ABSTRACT

A process for producing amorphous preparations of steryl glucoside monopalmitates, wherein steryl glucoside monopalmitates are heated at a temperature above 110° C up to about 145° C or the compounds are dissolved in an organic solvent in which they are soluble with a solvent which is then distilled off, and the compounds then pulverized and mixed with physiologically harmless organic or inorganic fine particles in a proportion of 0.5 times (by weight) of the compounds or more, thereby homogeneously dispersing the amorphous compounds in the fine particles or uniformtly adsorbing the compounds on the fine particles, and the resulting preparations which have hemostatic properties and are readily absorbable upon ingestion. The starting steryl glucoside monopalmitates are obtained in crystalline form as from soy beans or other vegetable sources.

7 Claims, 10 Drawing Figures

PROCESS FOR PRODUCING EASILY ABSORBABLE AMORPHOUS STERYL GLUCOSIDE MONOPALMITATES AND PREPARATIONS THEREOF

DESCRIPTION OF THE INVENTION

The present invention relates to a process for producing amorphous steryl glucoside monopalmitates and also to a process for producing amorphous preparations thereof which can be easily processed and can be easily absorbed. The steryl glucoside palmitates herein mean 6-monopalmitates of $\beta$-sitosteryl-$\beta$-D-glucoside, stigmasteryl-$\beta$-D-glucoside, compesteryl-$\beta$-D-glucoside, cholesteryl-$\beta$-D-glucoside and a mixture of various steryl-$\beta$-D-glucosides extracted from vegetables (hereinafter referred to as SGP). Said SGP widely exists together with other fatty acid esters in vegetables. They are obtained together with various fatty acid esters from natural substances such as soy beans, cotton seeds and rape-seeds according to, for example, a method of T. Kiribuchi, et al (Agr. Biol, Chem. Vol. 13, No. 8, 770–778 (1966). SGP is synthesized from steryl glucosides according to, for example, the method of T. Kiribuchi, et al (Agr. Biol. Chem., Vol, 31, No. 10, 1244–1247 (1967), said steryl glucosides being obtained from natural materials or obtained by a known process for steryl glucoside synthesis (for example, Chem. Ber. 105, 1097–1121). SGP having a strong hemostatic activity is a pharmacologically important substance.

All SGPs have approximately equal physical properties and characteristics. They are white flaky crystals easily soluble in nonpolar solvents such as chloroform, benzene and hexane, comparatively soluble in hot alcohol, hot acetone and esters and scarcely soluble in Macrogol (polyethyleneglycol), propylene glycol and water. Consequently, SGP itself is unsuitable for medicines in spite of its strong hemostatic activity, since absorbability thereof through the digestive tract upon ingestion is poor due to insolubility in water. This has been a recognized serious deficiency or disadvantage of SGP.

It is apparent from Table 2 hereinafter that original SGP powder obtained by pulverizing the crystalline SGP synthesized from steryl-$\beta$-D-glucoside extracted from soy beans (hereinafter referred to as SB-SGP) and then passing the same through a No. 100 sieve has a minimum effective dose of 64 mg/Kg ($P<0.05$), while aqueous SGP solution obtained by solubilizing the same powder with a surface active agent in ethanol has a minimum effective dose of 4 mg/Kg ($P<0.05$). Thus, it is evident that the pharmacological value and activity of SGP depends upon the solubility of SGP.

After intensive investigations on obtaining SGP preparations having a high absorbability through the digestive tract, the inventors have found by thermal analysis that SGP has polymorphism. It has been confirmed by thermal analysis, IR and X-ray diffraction that amorphous SGP can be obtained by keeping SGP crystals at an elevated temperature above 110° C., preferably at 125°–145° C. or by dissolving SGP crystals in an organic solvent and then distilling the solvent out. The inventors have further found that the amorphous SGP thus obtained exhibits the equivalent pharmacological activity in an amount of $\frac{1}{8}$–$\frac{1}{4}$ of the crystalline SGP. Amorphous SGP thus obtained by the heat treatment is in the form of glassy blocks, while SGP obtained by the treatment with solvent is in resinous form. Both must be pulverized before processing into preparations but mechanical pulverization is difficult because of their high coherence.

After further investigations regarding these problems, the inventors have found that amorphous SGP which can be processed easily into the desired preparations can be obtained by mixing SGP with organic or inorganic fine particles prior to the above described procedure in an amount of more than 0.5 times (by weight) of the SGP. The inventors have further found that the compositions thus obtained have a greatly increased absorbability through the digestive tract upon ingestion or administration orally.

The present invention has been realized on the basis of the above findings which are further particularized below:

(1) The process for producing amorphous SGP of high absorbability through the human digestive tracts is characterized in that stable crystalline SGP is either heated to a temperature of above 110° C. (preferably to 125°–145° C.) or dissolved once in a solvent in which SGP is soluble, and the solvent then distilled off.

(2) The process for producing amorphous SGP preparations of a high absorbability through the human or animal digestive tract which can be processed easily into medicinally valuable preparations, are characterized in that, in the production of the amorphous SGP according to (1), the SGP is admixed with physiologically harmless organic or inorganic fine particles in a necessary amount of more than 0.5 time (by weight) of SGP to disperse amorphous SGP in the fine particles homogeneously or to adsorb the former on the latter uniformly.

The heating time required for the transition from crystal form is equivalent both as to SGP alone and mixtures of SGP and powder particles. The time varies depending upon the heating temperature. At 125°–145° C., the heating time may be about 2–30 minutes. The solvent used is any low-boiling solvent in which SGP is soluble. Typical solvents are, for example, chloroform, dichloroethane, benzene and hexane. For the distillation of the solvent, reduced pressure distillation, spray-drying and freeze-drying, etc., are employed.

Typical fine particles to be mixed with SGP include organic substances such as starch, cellulose, lactose, polyvinyl pyrrolidone, methyl cellulose, Macrogol (polyethyleneglycol) and acacia and inorganic substances such as magnesium aluminate silicate, silicic acid anhydride, synthetic aluminum silicate, magnesium alumina hydroxide and aluminum hydroxide gel. These can be used either alone or in the form of mixtures of two or more of such substances. The proportion of the fine particles to SGP in the mixtures may range from about 0.5:1 (by weight) when the fine particles have a large bulk or a high absorbability, to about 10:1 when the fine particles have a small bulk. However, the proportion is not limited to this range. The amorphous SGP preparations thus obtained can be used without any further treatment or may be diluted with other powders to easily produce compound powders, capsules, tablets, etc., and other bulk or unit dosage orally administrable forms.

It is apparent that the pharmacological activity of steryl glucoside monopalmitate appears two hours after administration, according to data obtained by a method of determining pharmacological activity proposed by Motohashi, et al. (Journal of Tokyo Jikei-Kai Medical College 75 (5), 1008 (1959), wherein hemostatic activity on the small arteries at the end of a tail of a mouse is observed as shown in Table 1 which follows. Accordingly, differences in the pharmacological activities of typical compositions of the present invention were examined two hours after the oral administration. The results are set forth in Table 2.

Table 1

Change in manifestation of pharmacological effect after the administration of 64 mg/Kg of crystalline SB steryl-$\beta$-D-glucoside monopalmitate

| | Hemostatic time | Significant difference |
|---|---|---|
| Control | 13.8 ± 1.1 min | — |
| One hour after administration | 11.2 ± 1.0 min | — |
| Two hours after administration | 10.0 ± 1.0 min | ($p < 0.05$) |
| Three hours after administration | 10.8 ± 1.2 min | — |
| Four hours after administration | 11.5 ± 1.3 min | — |

Table 2

| | Steryl glucoside | Fine particles | Production Process | 128 | 64 | 32 | Hemostatic Activity Dose mg/Kg in mouse 16 | 8 | 4 | 2 | Control |
|---|---|---|---|---|---|---|---|---|---|---|---|
| 1. | β-sitosteryl monopalmitate | — | Original powder (crystalline) | | 8.6 ± 1.1* min | 9.8 ± 1.5 min | | | | | 12.8 ± 1.3 min |
| 2. | Stigmasteryl-β-D-GP | — | " | | 9.0 ± 1.0* | 10.2 ± 1.3 | | | | | 12.8 ± 1.3 |
| 3. | Cholesteryl-β-D-GP | — | " | | 9.9 ± 1.1 | 10.5 ± 1.1 | | | | | 12.8 ± 1.3 |
| 4. | SB-Steryl-β-D-GP | — | " | 8.8 ± 1.3* min | | | | | | | 12.8 ± 1.3 |
| 5. | SB-Steryl-β-D-GP | — | 100 mg of the original powder are dissolved in 5 ml of ethanol and 4 g of HCO-60 and then diluted with water into 100 ml. | | 8.8 ± 1.2* | 10.0 ± 1.0 | | 8.1 ± 1.0** min | 9.0 ± 1.2* min | 9.9 ± 1.0 min | 12.8 ± 1.3 |
| 6. | SB-Steryl-β-D-GP | — | Example 1 | | | 8.8 ± 0.8* | 9.7 ± 1.6 min | | | | 12.8 ± 1.3 |
| 7. | SB-Steryl-β-D-GP | — | Example 2 | | | 8.0 ± 1.0** | 9.1 ± 0.9* | 9.9 ± 1.5 | | | 12.8 ± 1.3 |
| 8. | SB-Steryl-β-D-GP | Magnesium aluminate silicate | Example 3 (50% powder) | | | | 9.4 ± 1.0* | 10.0 ± 1.1 | | | 12.8 ± 1.3 |
| 9. | SB-Steryl-β-D-GP | " | Example 4 (50% powder) | | | | 8.0 ± 0.8** | 9.2 ± 1.1* | 10.0 ± 1.1 | | 12.6 ± 0.9 |
| 10. | SB-Steryl-β-D-GP | " | Simple mixing (50% powder) | | 9.3 ± 1.2* | 10.3 ± 1.1 | | | | | 13.1 ± 1.2 |
| 11. | Stigmasteryl-β-D-GP | — | According to Example 1 | | | 9.1 ± 1.0* | 9.7 ± 1.3 | | | | 13.1 ± 1.2 |
| 12. | Cholesteryl-β-D-GP | — | According to Example 2 | | 9.4 ± 1.0* | 9.8 ± 1.1 | 9.7 ± 1.2 | | | | 13.1 ± 1.2 |
| 13. | Sitosteryl-β-D-GP | — | | | | 8.1 ± 0.9** | | | | | 13.1 ± 1.2 |
| 14. | β-Sitosteryl-β-D-GP | Corn starch | According to Example 3 (10% powder) | | | | 9.5 ± 0.9* | 10.1 ± 1.2 | | | 13.1 ± 1.2 |
| 15. | SB-Steryl-β-D-GP | Polyvinyl pyrrolidone (molecular weight: 4 × 10⁴) | According to Example 3 (10% powder) | | | | 8.1 ± 1.2** | 9.9 ± 1.5 | | | 13.1 ± 1.2 |
| 16. | SB-Steryl-β-D-GP | Magnesium alumina hydroxide | According to Example 3 (20% powder) | | | | 9.0 ± 1.1* | 10.4 ± 1.2 | | | 13.1 ± 1.2 |
| 17. | SB-Steryl-β-D-GP | Synthetic aluminum silicate | According to Example 3 (20% powder) | | | | 9.3 ± 0.9* | 10.0 ± 1.0 | | | 13.1 ± 1.2 |
| 18. | SB-Steryl-β-D-GP | Macrogoal 6000 | According to Example 4 (10% powder) | | | | 6.9 ± 0.8** | 8.5 ± 0.8** | 10.3 ± 1.2 | | 12.6 ± 0.9 |
| 19. | Stigmasteryl-β-D-GP | Microcrystalline cellulose | According to Example 4 (20% powder) | | | | 8.0 ± 0.8** | 9.2 ± 1.1* | 9.5 ± 1.1 | | 12.6 ± 0.9 |
| 20. | SB-Steryl-β-D-GP | Silicic acid anhydride | According to Example 4 (50% powder) | | | | 8.7 ± 0.8** | 9.5 ± 1.0* | 9.8 ± 1.2 | | 12.6 ± 0.9 |
| 21. | SB-Steryl-β-D-GP | Aluminum hydroxide gel | According to Example 4 (20% powder) | | | | 8.6 ± 1.0** | 9.2 ± 1.0** | 10.1 ± 1.2 | | 12.6 ± 0.9 |

**(P < 0.01)
*(P < 0.05)

The invention is illustrated below by the following non-limitative examples.

EXAMPLE 1

Figure 1:
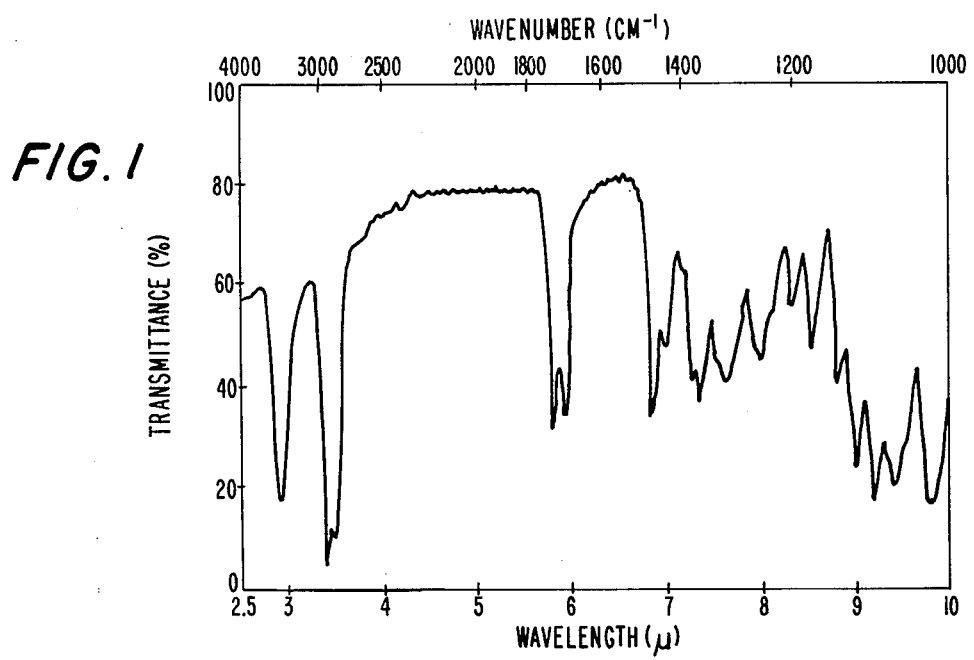
FIG. 1 is an IR chart of crystalline steryl glucoside monopalmitate.
Figure 2:
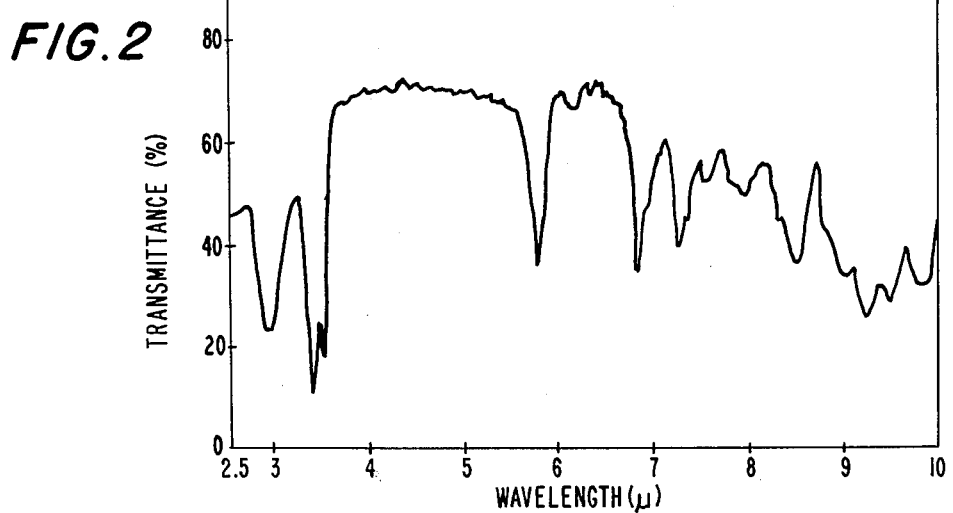
FIGS. 2, 3, 4 and 5 are IR charts of amorphous compounds obtained by the present invention.
Figure 6:
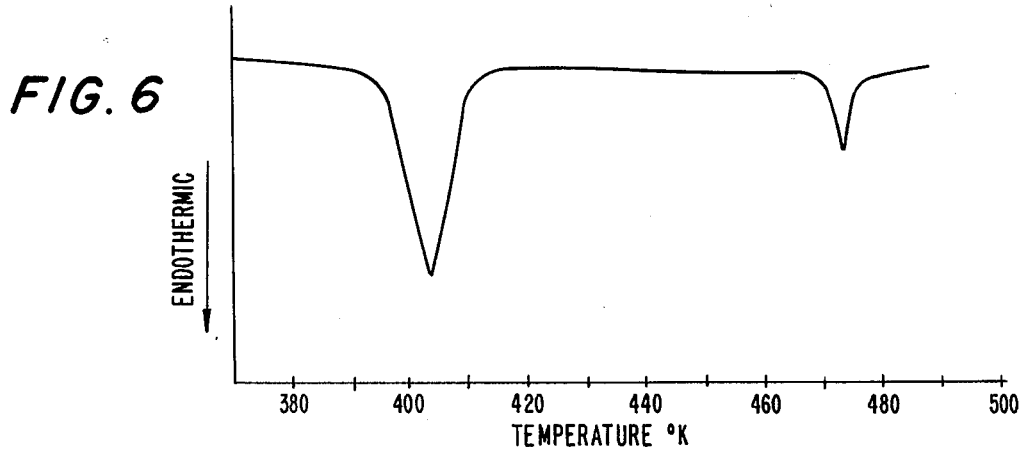
FIG. 6 is a differential thermal analysis chart of crystalline steryl glucoside monopalmitate.
Figure 7:
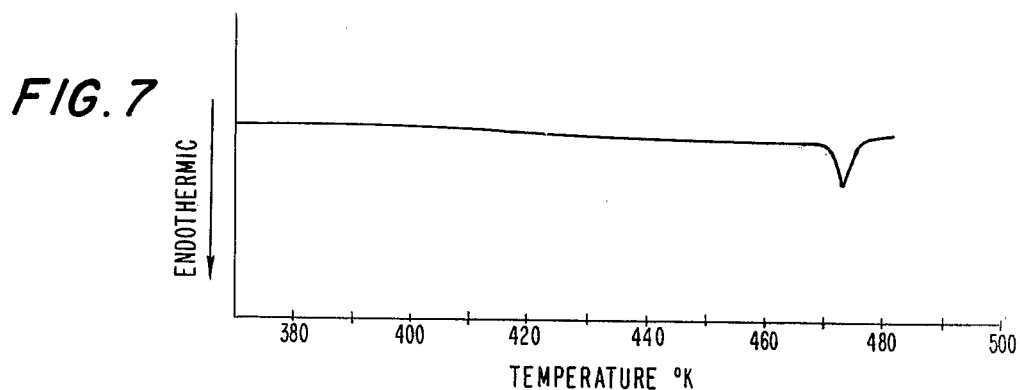
FIGS. 7, 8, 9 and 10 are differential thermal analysis charts of the amorphous products obtained by the present invention.

Crystalline SB-SGP was heated to 130° C. in an oven for 15 minutes and then allowed to cool to room temperature to obtain a semi-transparent glassy amorphous product. IR Charts of the crystalline and amorphous substances determined with a Leitz infrared spectrophotometer are shown in FIGS. 1 and 2. Comparing FIG. 1 with FIG. 2, it was apparent that crystalline SB-SGP had two peaks at 1688 cm$^{-1}$ and 1771 cm$^{-1}$ (carbonyl), while the heat-treated product had only one peak at 1754 cm$^{-1}$ to clearly indicate the transition in crystal form. Results of differential thermal analysis with Perkin-Elmer Model DSC-II under conditions of a temperature program rate of 10° C./min., a range of 1mCal./sec. and a chart speed of 20 mn/min. are shown in FIG. 6 (chart of crystalline SB-SGP) and FIG. 7 (chart of amorphous product). It is apparent therefrom that absorption due to heat of transition at around 130° C. disappeared due to the heat treatment, thereby indicating the conversion into a high temperature stable phase (unstable at low temperatures). The amorphous product thus obtained was pulverized by a suitable method and the powders were passed through a No. 100 sieve. Pharmacological activity of the powdery product that passed through the sieve was examined to reveal that it exhibited an activity equivalent to ¼ dose of crystalline SB-SGP.

EXAMPLE 2

Figure 3:
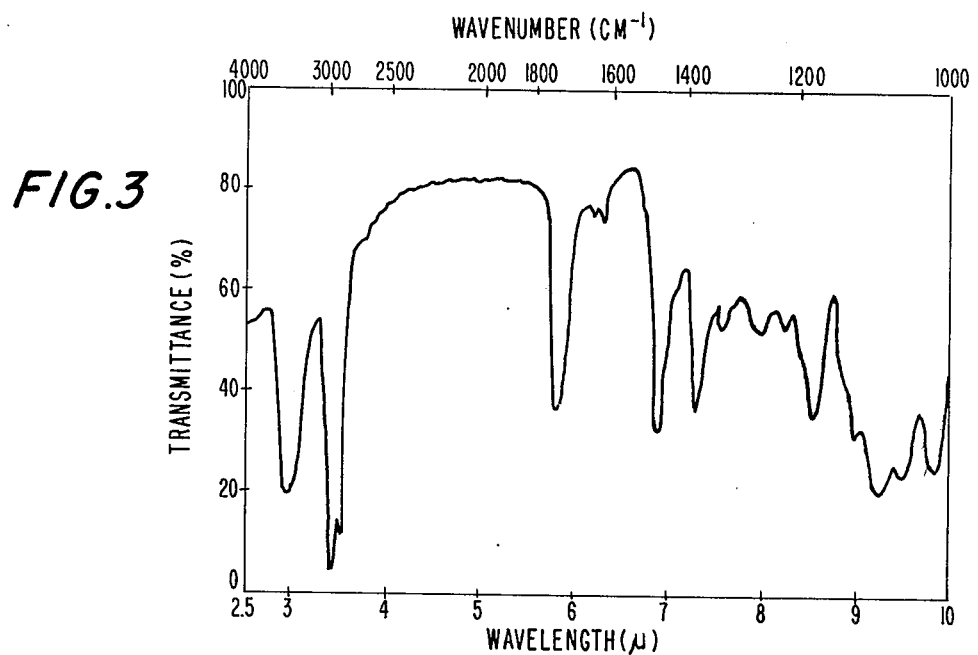
Figure 8:
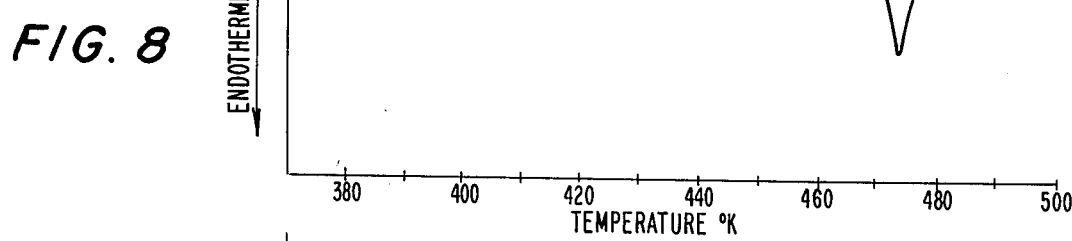

One gram of crystalline SB-SGP was dissolved in 8 ml of chloroform and the solvent was then distilled off with a rotary evaporator to yield an amorphous product. An IR Chart and the results of differential thermal analysis are shown in FIGS. 3 and 8, respectively.

The chart characteristics showed as similar to those of the amorphous product obtained in Example 1 to reveal than an amorphous product was formed in this example. The amorphous product thus obtained was scraped off from the vessel and passed through a No. 100 sieve. The pharmacological activity of the particles that passed through the sieve was examined to reveal that the pharmacological effect was equivalent to ¼ the dose of the crystalline SB-SGP.

EXAMPLE 3

Figure 4:
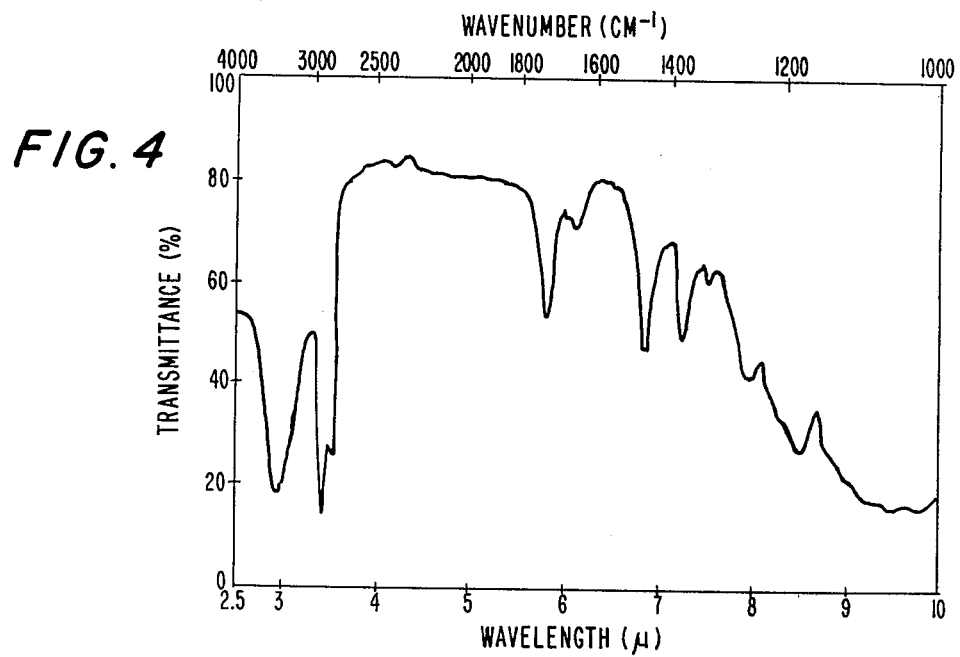
Figure 9:
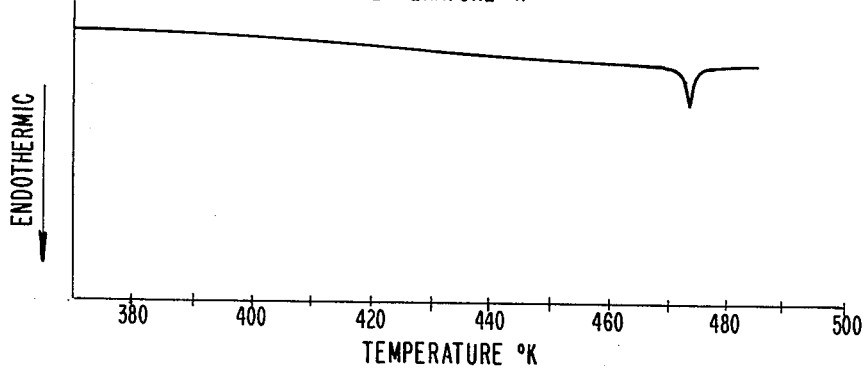

One gram of SB-SGP and 1 g of magnesium aluminate silicate were mixed together in a motor to obtain the homogeneous mixture. The mixture was heated to 135° C. in an oven for 10 minutes and allowed to cool at room temperature to obtain homogeneous dispersion of the amorphous product in the fine particles. An IR Chart and differential thermal analysis chart are shown in FIGS. 4 and 9, respectively. Magnesium aluminate silicate did not exert any influence on the carbonyl absorption band of SB-SGP. These charts exhibited characteristics similar to those of the amorphous product produced in Example 1. Thus, it was apparent that the amorphous product was obtained in this example. Pharmacological activity of the composition was examined to reveal that the pharmacological effect was equivalent to ¼ the dose of the crystalline SB-SGP.

EXAMPLE 4

Figure 5:
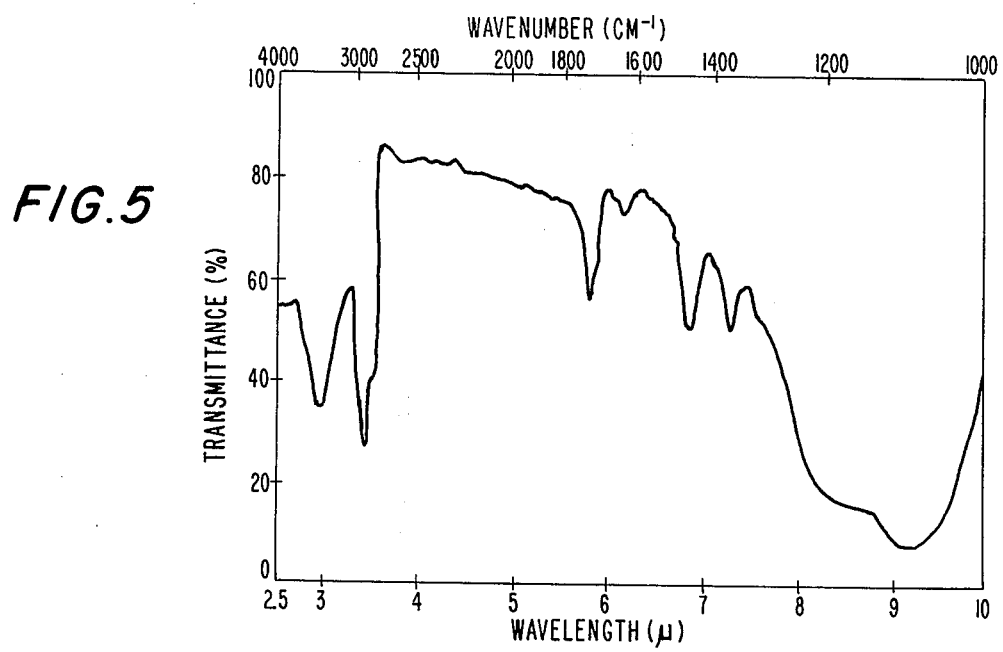
Figure 10:
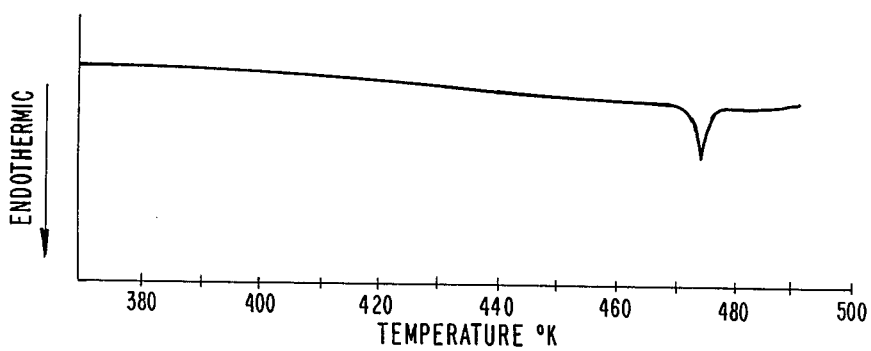

One gram of SB-SGP was dissolved in 15 ml. of chloroform. To the solution was added 1 g of magnesium aluminate silicate. Chloroform was distilled off with a rotary evaporator to obtain an amorphous product uniformly adsorbed on the fine particles. An IR Chart and differential thermal analysis chart are shown in FIGS. 5 and 10, respectively. These charts had characteristics similar to those of the amorphous product produced in Example 1. Thus, it was apparent that the amorphous product was obtained in this example. Pharmacological activity of the composition was determined to reveal that the pharmacological effect was equivalent to ¼ the dose of the crystalline SB-SGP.

What is claimed is:

1. A process for the production of pharmaceutical composition having hemostatic activity which comprises converting a crystalline steryl glucoside monopalmitate to amorphous form by heating it to a temperature above 110° C. and in the range of 125°–145° C. and for a period of time of about 2–30 minutes to effect such conversion or by dissolving the crystalline steryl glucoside monopalmitate in an organic solvent in which it is soluble and distilling off the solvent, and admixing the thus formed amorphous steryl glucoside monopalmitate with physiologically harmless organic or inorganic fine particles to form a homogeneous dispersion having enhanced absorbability upon ingestion or administration and in which the amorphous steryl glucoside monopalmitate is absorbed on or dispersed in the physiologically harmless organic or inorganic fine particles in the proportion of at least 0.5 parts per part of steryl glucoside monopalmitate, by weight.

2. A process according to claim 1 wherein 0.5 to 10 parts of the fine particles are admixed with one part of the steryl glucoside monopalmitate, by weight.

3. A process according to claim 1 wherein the fine particles are selected from starch, cellulose, lactose, polyvinyl pyrrolidone, methyl cellulose, polyethyleneglycol, acacia, magnesium aluminate silicate, silicic acid anhydride, synthetic aluminum silicate, magnesium alumina hydroxide and aluminum hydroxide gel, individually and in mixtures thereof.

4. A method according to claim 1 wherein the fine particles are selected from starch, cellulose, lactose, polyvinyl pyrrolidone, methyl cellulose, polyethyleneglycol, acacia, magnesium aluminate silicate, silicic acid anhydride, synthetic aluminum silicate, magnesium alumina hydroxide and aluminum hydroxide gel, individually and in mixtures thereof and the steryl glucoside monopalmitate is selected from a 6-monopalmitate of β-sitosteryl-β-D-glucoside, stigmasteryl-β-D-glucoside, compesteryl-β-D-glucoside, or cholesteryl-β-D-glucoside.

5. A pharmaceutical composition having hemostatic activity comprising an amorphous steryl glucoside monopalmitate obtained from a crystalline steryl glucoside monopalmitate and adsorbed on or dispersed in physiologically harmless fine organic or inorganic particles, the said composition having enhanced absorbability upon ingestion or administration and the proportion of fine particles to steryl glucoside monopalmitate being from 0.5:1 to 10:1, by weight.

6. A pharmaceutical composition according to claim 5 wherein the steryl glucoside monopalmitate is a 6-monopalmitate of β-sitosteryl-β-D-glucoside, stigmasteryl-β-D-glucoside, compesteryl-β-D-glucoside, or cholesteryl-β-D-glucoside.

7. A pharmaceutical composition according to claim 5 wherein the fine particles are selected from starch, cellulose, lactose, polyvinyl pyrrolidone, methyl cellulose, polyethyleneglycol, acacia, magnesium aluminate silicate, silicic acid anhydride, synthetic aluminum silicate, magnesium alumina hydroxide and aluminum hydroxide gel, individually and in mixtures thereof.

* * * * *